(12) United States Patent
Arakawa et al.

(10) Patent No.: US 12,239,437 B2
(45) Date of Patent: Mar. 4, 2025

(54) DEVICE, METHOD, AND PROGRAM FOR DETERMINING PARAMETER INDICATING SHAPE OF EAR CANAL BASED ON LAYERS PERPENDICULAR TO CALCULATED CENTER LINE OF EAR CANAL

(71) Applicant: NEC Corporation, Tokyo (JP)

(72) Inventors: Takayuki Arakawa, Tokyo (JP); Yoshitaka Ito, Tokyo (JP)

(73) Assignee: NEC CORPORATION, Tokyo (JP)

( * ) Notice: Subject to any disclaimer, the term of this patent is extended or adjusted under 35 U.S.C. 154(b) by 358 days.

(21) Appl. No.: 17/783,699

(22) PCT Filed: Dec. 13, 2019

(86) PCT No.: PCT/JP2019/048845
§ 371 (c)(1),
(2) Date: Jun. 9, 2022

(87) PCT Pub. No.: WO2021/117206
PCT Pub. Date: Jun. 17, 2021

(65) Prior Publication Data
US 2023/0027011 A1    Jan. 26, 2023

(51) Int. Cl.
*A61B 5/1171* (2016.01)
*G01B 17/06* (2006.01)
(Continued)

(52) U.S. Cl.
CPC ............ *A61B 5/1171* (2016.02); *G01B 17/06* (2013.01); *G01B 21/14* (2013.01); *G06T 7/0012* (2013.01);
(Continued)

(58) Field of Classification Search
CPC ...... A61B 5/1171; G06V 40/00; G06V 40/10; G01B 17/06; G01B 21/14; G06T 7/0012;
(Continued)

(56) References Cited

U.S. PATENT DOCUMENTS 10,878,563 B2 * 12/2020 Nakagawa ........... H04R 25/652
10,897,676 B2 *  1/2021 Wagner ................. H04R 25/60
(Continued)

FOREIGN PATENT DOCUMENTS

CN       108013892 B  *  6/2021    ............. A61B 6/032
EP       2003598 A1  * 12/2008    ......... G06K 9/00362
(Continued)

OTHER PUBLICATIONS

Balouch, Auden P., et al. "Measurements of ear-canal geometry from high-resolution CT scans of human adult ears." Hearing Research 434 (2023): 108782. (Year: 2023).*
(Continued)

*Primary Examiner* — Scott A Rogers

(57) ABSTRACT

To easily evaluate the performance of an earphone-type device used for otoacoustic authentication at low cost.
A generation unit (31) generates earhole shape data indicating the three-dimensional shape of an individual's ear canal, on the basis of data on the internal structure of an individual's earhole, a center line calculation unit (32) calculates the center line of the ear canal, on the basis of the ear canal shape data, and a dividing unit (33) divides the ear canal into a plurality of layers perpendicular to the center line, and calculates, for each of the divided layers, parameters indicating the shape of the ear canal.

6 Claims, 13 Drawing Sheets

(51) Int. Cl.
*G01B 21/14* (2006.01)
*G06T 7/00* (2017.01)
*G06V 40/10* (2022.01)

(52) U.S. Cl.
CPC .... *G06V 40/10* (2022.01); *G06T 2207/10072* (2013.01)

(58) Field of Classification Search
CPC .............. G06T 7/12; G06T 2207/10072; G06T 2207/10081
See application file for complete search history.

(56) References Cited

U.S. PATENT DOCUMENTS

| | | | |
|---|---|---|---|
| 2009/0097724 A1 | 4/2009 | McBagonluri et al. | |
| 2010/0100362 A1* | 4/2010 | Zouhar | H04R 25/658 703/2 |
| 2024/0169747 A1* | 5/2024 | Jobin | B33Y 80/00 |

FOREIGN PATENT DOCUMENTS

| | | | | |
|---|---|---|---|---|
| EP | 2180428 A2 * | 4/2010 | ......... | G06K 9/00201 |
| JP | 2005-535017 A | 11/2005 | | |
| JP | 2006-326292 A | 12/2006 | | |
| JP | 7236689 B2 * | 3/2023 | ........... | G06T 7/0012 |
| WO | 2013/172039 A1 | 11/2013 | | |
| WO | 2017/069118 A1 | 4/2017 | | |

OTHER PUBLICATIONS

Decraemer, W. F., J. J. J. Dirckx, and W. R. J. Funnell. "Three-dimensional modelling of the middle-ear ossicular chain using a commercial high-resolution X-ray CT scanner." Journal of the Association for Research in Otolaryngology 4 (2003): 250-263. (Year: 2003).*

Hussain, Raabid, et al. "Automatic segmentation of inner ear on CT-scan using auto-context convolutional neural network." Scientific Reports 11.1 (2021): 4406. (Year: 2021).*

Lee, Chia-Fone, et al. "Three dimensional reconstruction and modeling of middle ear biomechanics by high resolution computed tomography and finite element analysis." The Laryngoscope 116.5 (2006): 711-716. (Year: 2006).*

Poznyakovskiy, Anton A., et al. "The creation of geometric three-dimensional models of the inner ear based on micro computer tomography data." Hearing research 243.1-2 (2008): 95-104. (Year: 2008).*

International Search Report for PCT Application No. PCT/JP2019/048845, mailed on Feb. 25, 2020.

English translation of Written opinion for PCT Application No. PCT/JP2019/048845, mailed on Feb. 25, 2020.

Christopher M. Bishop, "Pattern Recognition and Machine Learning", Springer Science + Business Media, LLC, Chapter 4, pp. 179-224, Feb. 15, 2010.

* cited by examiner

Fig.10

| ACOUSTIC CHARACTERISTIC DATA OF EAR MODEL | | |
|---|---|---|
| PARAMETER | | |
| DIAMETER SIZE OF HOLE (R) | NUMBER (n) OF PLATE-SHAPED MEMBER | |
| 5[mm] | 1 | DATA OF TRANSFER FUNCTION |
| 5[mm] | 2 | |
| 10[mm] | 3 | |
| 10[mm] | 4 | |
| 15[mm] | 5 | |
| 20[mm] | 6 | |

DEVICE, METHOD, AND PROGRAM FOR DETERMINING PARAMETER INDICATING SHAPE OF EAR CANAL BASED ON LAYERS PERPENDICULAR TO CALCULATED CENTER LINE OF EAR CANAL

This application is a National Stage Entry of PCT/JP2019/048845 filed on Dec. 13, 2019, the contents of all of which are incorporated herein by reference, in their entirety.

TECHNICAL FIELD

The disclosure relates to a parameter determination device, a parameter determination method, and a recording medium, and particularly relates to a parameter determination device, a parameter determination method, and a recording medium that determine a parameter of an ear model in a personal authentication technology based on personal characteristics of a shape of an ear hole of a human.

BACKGROUND ART

For example, fingerprint authentication, vein authentication, face authentication, iris authentication, and voice authentication are known as personal authentication technology (referred to as biometric authentication technology) based on personal characteristics of a living body. Among the personal authentication technologies, in particular, the otoacoustic authentication focuses on a personal characteristic of an internal structure of a human ear hole. In the otoacoustic authentication, an inspection signal is input to an ear hole of an individual to be authenticated, and personal authentication is performed using an echo signal based on an echo sound from the ear hole.

An individual (person to be authenticated) to be subjected to personal authentication wears a device (referred to as an earphone-type device or a hearable device) having an earphone shape with a built-in speaker and microphone on the auricle. The speaker of the earphone-type device transmits an inspection signal (sound wave) toward the inside of the ear hole of the person to be authenticated. The microphone of the earphone-type device collects echo sound from the ear hole. Then, an echo signal based on the echo sound is transmitted from the earphone-type device to the personal authentication device. The personal authentication device performs personal authentication by checking the echo signals of one or more individuals registered in advance against the echo signal received from the earphone-type device.

The otoacoustic authentication technology has advantages that the personal authentication is instantaneously and stably completed, that even when an individual is moving or working, the personal authentication can be immediately performed while the individual wears the earphone-type device (hands-free), and that confidentiality regarding the internal structure of the human ear hole is high.

CITATION LIST

Patent Literature

[PTL 1]: WO 2017/069118 A
[PTL 2]: WO 2013/172039 A
[PTL 3] JP 2005-535017 A

Non Patent Literature

[Non Patent Literature 1] "PATTERN RECOGNITION AND MACHINE LEARNING" (CHRISTOPHER M. BISHOP) (Springer Science+Business Media, LLC) (2010, Feb. 15)

SUMMARY OF INVENTION

Technical Problem

In a related otoacoustic authentication technology, performance evaluation of an earphone-type device is performed. Specifically, a plurality of subjects is caused to wear the same earphone-type device in order, and the otoacoustic authentication is tested, and a false rejection rate (FRR) and a false acceptance rate (FAR), which are index values of performance of the earphone-type device, are calculated. However, since it is necessary to restrain the subjects for a long time in order to accurately evaluate the performance of the earphone-type device, there is a problem that time and effort for performance evaluation are large and cost is high.

The disclosure has been made in view of the above problems, and an object of the disclosure is to provide a technique for evaluating performance of an earphone-type device used for otoacoustic authentication easily and at a low cost.

Solution to Problem

A parameter determination device according to an aspect of the disclosure includes a generation means configured to generate, based on data regarding an internal structure of an ear hole of an individual, shape of ear hole data indicating a three-dimensional shape of an ear canal of the individual, a center line calculation means configured to calculate a center line of the ear canal based on the shape of ear hole data, and a dividing means configured to divide the ear canal into a plurality of layers perpendicular to the center line and calculate a parameter indicating a shape of the ear canal for each of the divided layers.

A parameter determination method according to an aspect of the disclosure includes generating, based on data regarding an internal structure of an ear hole of an individual, shape of ear hole data indicating a three-dimensional shape of an ear canal of the individual, calculating a center line of the ear canal based on the shape of ear hole data, and dividing the ear canal into a plurality of layers perpendicular to the center line and calculating a parameter indicating a shape of the ear canal for each of the divided layers.

A non-transitory recording medium according to an aspect of the disclosure stores a program for causing a computer to execute a step of generating, based on data regarding an internal structure of an ear hole of an individual, shape of ear hole data indicating a three-dimensional shape of an ear canal of the individual, a step of calculating a center line of the ear canal based on the shape of ear hole data, and a step of dividing the ear canal into a plurality of layers perpendicular to the center line and calculating a parameter indicating a shape of the ear canal for each of the divided layers.

Advantageous Effects of Invention

According to an aspect of the disclosure, it is possible to easily and inexpensively evaluate the performance of an earphone-type device used for otoacoustic authentication.

BRIEF DESCRIPTION OF DRAWINGS

FIG. 10 is a diagram illustrating an example of acoustic characteristic data of an ear model output by an arithmetic device included in the system according to the first example embodiment.

EXAMPLE EMBODIMENT

Hereinafter, a method for manufacturing an ear model for evaluating the performance of an earphone-type device used for the otoacoustic authentication easily and at low cost will be described.

First Example Embodiment

A first example embodiment will be described below with reference to FIGS. 1 to 10.
(System 1)

Figure 1:
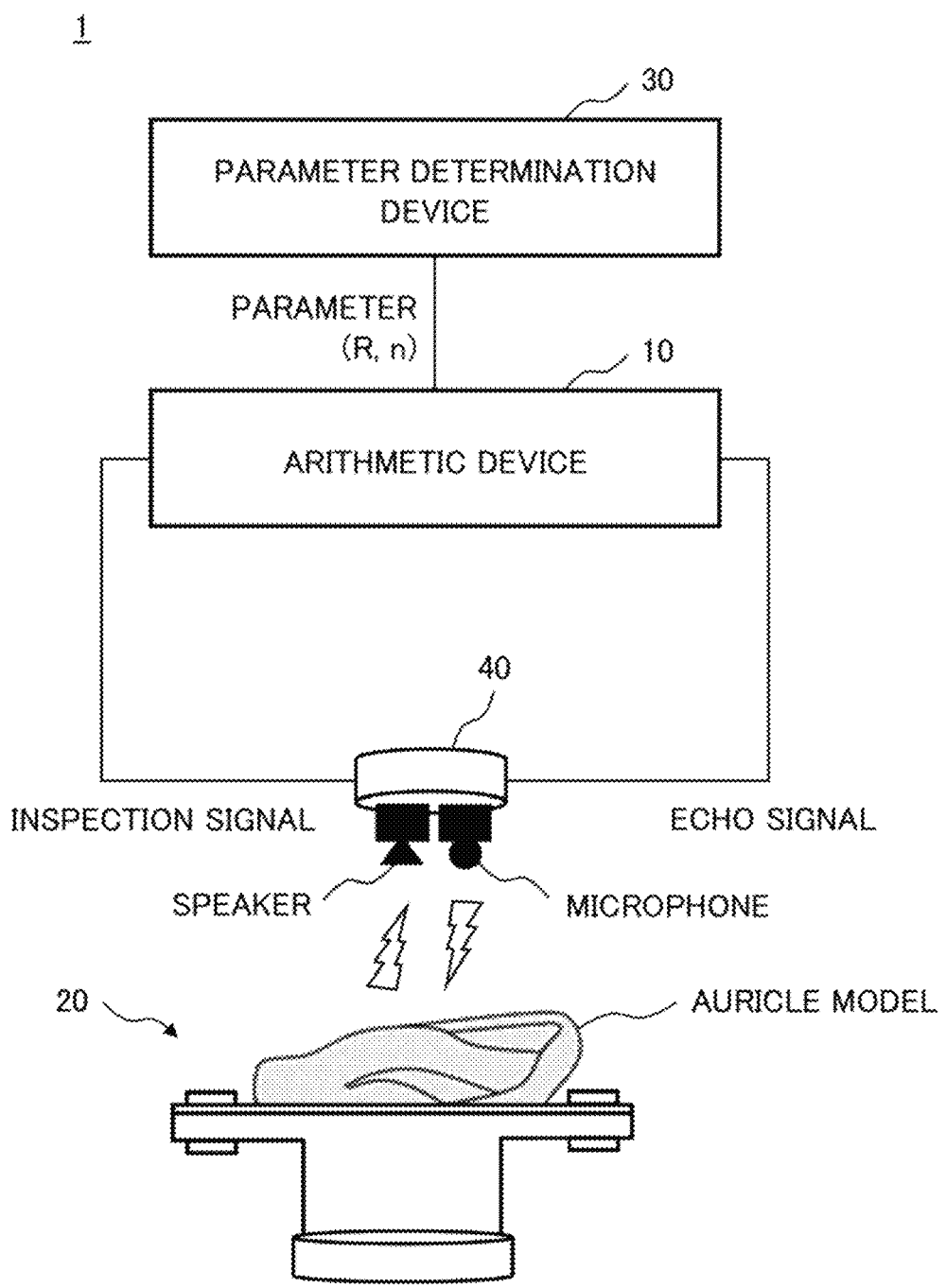
FIG. 1 is a schematic diagram illustrating a configuration of a system according to a first example embodiment.

FIG. 1 is an example of a system 1 according to the first example embodiment. As illustrated in FIG. 1, the system 1 includes an arithmetic device 10, an ear model 20, a parameter determination device 30, and an earphone-type device 40.

FIG. 1 illustrates an appearance of the ear model 20. The ear model 20 simulates an internal structure of an ear hole of an individual. More specifically, a hole is provided in the ear model 20, and this hole simulates at least an internal structure (hereinafter, referred to as an ear canal) from the ear canal opening to the eardrum in the ear hole of an individual (the hole of the ear model 20 will be described later). An auricle model is placed on the ear model 20. The auricle model is made to match the shape of the earphone-type device 40 (FIG. 1). For example, the auricle model is produced by taking a mold of an individual's auricle and pouring a material such as silicone rubber of a fluid into the mold. Alternatively, the auricle of an individual may be scanned to generate 3D data of the auricle, and an auricle model may be produced by a 3D printer technology based on the generated 3D data of the auricle.
(Earphone-Type Device 40)

The earphone-type device 40 incorporates at least a speaker and a microphone. However, in FIG. 1, a speaker and a microphone built in the earphone-type device 40 are schematically illustrated on the surface of the earphone-type device 40. The earphone-type device 40 is worn in such a way as to be embedded in a portion related to the ear hole opening of the auricle model. The earphone-type device 40 is connected to an arithmetic device (not illustrated) in a wireless or wired manner.

The earphone-type device 40 receives an instruction to transmit an inspection signal from an arithmetic device (not illustrated). The earphone-type device 40 transmits an inspection signal from a speaker built in the earphone-type device 40 to the inside of the hole of the ear model 20 via the ear hole opening provided in the auricle model. The earphone-type device 40 collects by the microphone an echo sound transmitted from the ear model 20 after the inspection signal propagates in the ear model 20. The earphone-type device 40 generates an echo signal based on an echo sound collected by the microphone to transmit the echo signal to an arithmetic device (not illustrated).
(Ear Model 20a)

Figure 2:
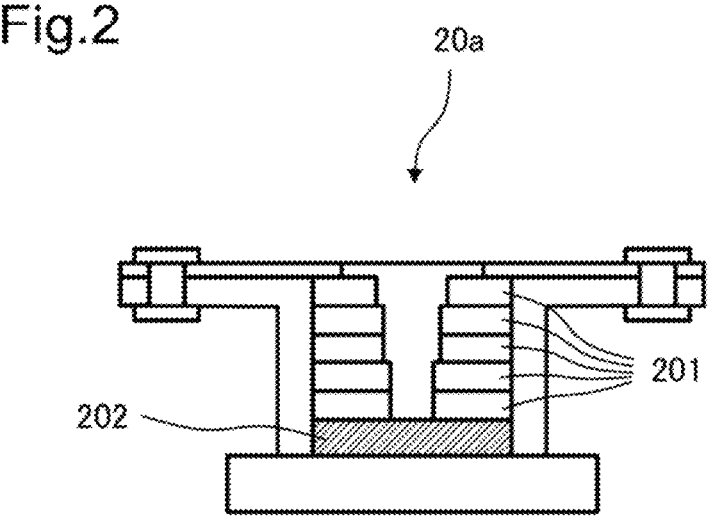
FIG. 2 is a cross-sectional view of an example of an ear model included in the system according to the first example embodiment.

FIG. 2 is a cross-sectional view of an ear model 20a that is an example of the ear model 20 illustrated in FIG. 1. As illustrated in FIG. 2, the ear model 20a according to the first example embodiment includes at least a plurality of plate-shaped members 201 and one artificial eardrum member 202. In FIG. 2, illustration of an auricle model (also referred to as an artificial auricle) on the ear model 20a is omitted.

The upper face of the ear model 20a illustrated in FIG. 2 corresponds to a face on which the auricle model is disposed in FIG. 1. The hole of the plate-shaped member 201 located on the uppermost surface of the ear model 20a corresponds to an ear canal opening of an individual. The internal structure (specifically, the ear canal) of the ear hole of an individual is simulated by connecting the holes provided at the centers of the plurality of plate-shaped members 201 from the upper face of the ear model 20a (the surface in contact with the auricle model) to the artificial eardrum member 202. The plurality of plate-shaped members 201 is stacked and accommodated in a hollow cylinder. In the hollow cylinder, the upper plate-shaped members 201 are in close contact with the lower plate-shaped members 201 (or the artificial eardrum member 202) by its own weight and the weight of the upper plate-shaped member 201.

Figure 3:
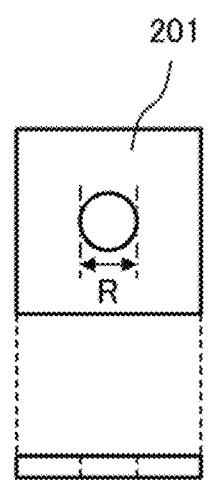
FIG. 3 is a view illustrating a shape of a plate-shaped member included in the ear model according to the first example embodiment.

FIG. 3 illustrates a shape of the plate-shaped member 201 constituting the ear model 20a. As illustrated in FIG. 3, a hole penetrating through the plate-shaped member 201 in the thickness direction is provided at the center of the plate-shaped member 201. The thickness of the plate-shaped member 201 is, for example, 5 mm. The size (R) of the diameter of the hole is variable, for example, between 5 mm and 20 mm. The plate-shaped member 201 is made of, for example, acrylic. However, the material of the plate-shaped member 201 is not particularly limited. In general, the acoustic characteristics of the ear holes depend on length and thickness, but not on the complexity of the curvature of the ear hole. The acoustic characteristics of the ear hole do not depend on the material or texture (hardness) of the inner wall of the ear hole. Therefore, even when the ear model 20a is formed of the plate-shaped member 201 having a material or texture different from that of the human ear, or even when the plurality of plate-shaped members 201 is linearly disposed, it has the acoustic characteristics substantially equivalent to those of the ear hole of an individual having the same length and thickness as those of the hole of the ear model 20a.

In the ear model 20a, the plurality of plate-shaped members 201 is stacked in an arrangement order according to the number (n) assigned to each plate-shaped member 201 in advance. The sizes (R) of the holes of the plurality of plate-shaped members 201 and the number (n) indicating the arrangement order are determined based on the internal structure of the ear hole of an individual to be simulated by the ear model 20a.

The thickness and the number of the plurality of plate-shaped members 201 constituting the ear model 20a relates to the length from the ear canal opening to the eardrum of an individual (simulated by the internal structure of the hole of the ear model 20a).

The size of the diameter of the hole provided in each of the plurality of plate-shaped members 201 constituting the ear model 20a relates to a thickness of the ear canal of an individual (simulated by the internal structure of the hole of the ear model 20a).

Data (hereinafter, it is referred to as shape of ear hole data) regarding the internal structure of the ear hole of an individual is obtained by, for example, computed tomography (CT) scan. In an example, the parameter (R, n) of the ear model 20a is obtained as follows from the result of performing the CT scan on the subject.

(Parameter Determination Device 30)

Figure 4:
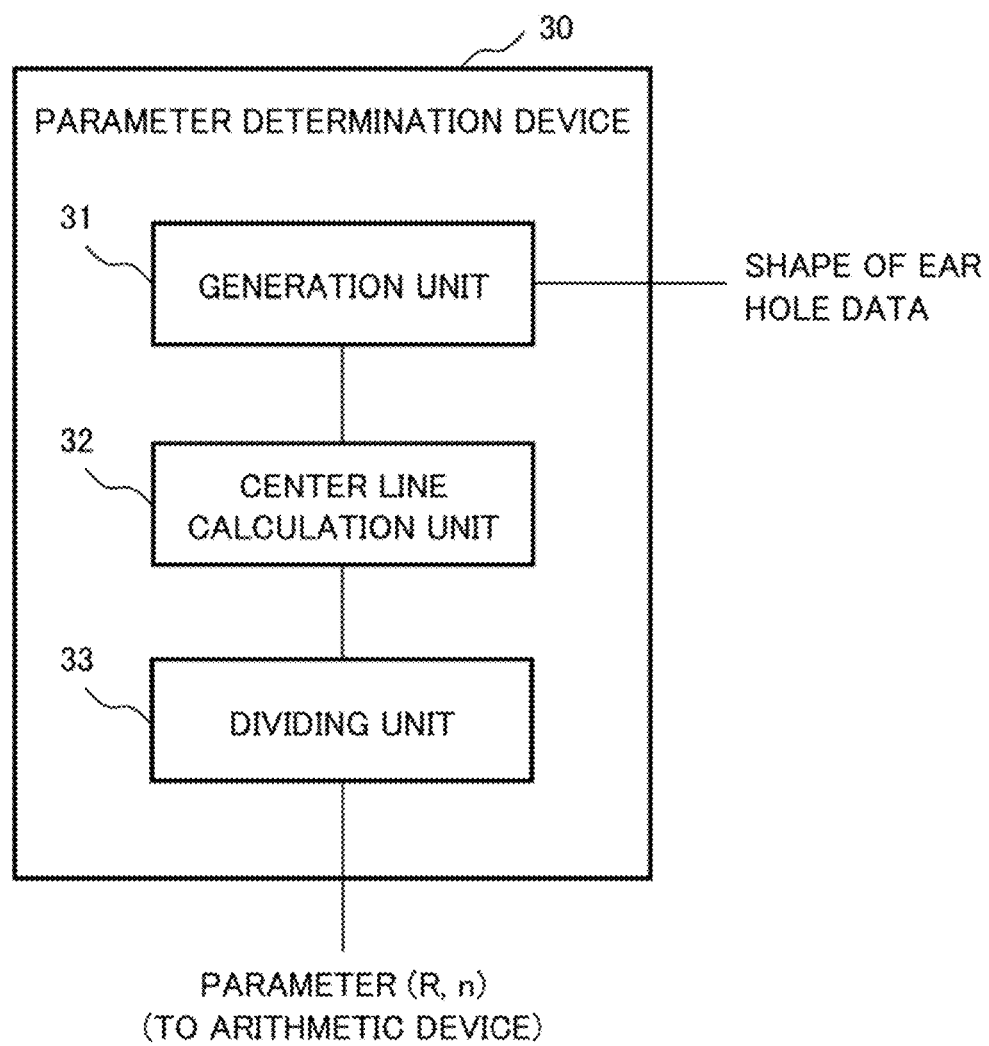
FIG. 4 is a block diagram illustrating a configuration of a parameter determination device according to the first example embodiment.

A configuration of the parameter determination device 30 according to the first example embodiment will be described with reference to FIG. 4. FIG. 4 is a block diagram illustrating a configuration of the parameter determination device 30.

As illustrated in FIG. 4, the parameter determination device 30 includes a generation unit 31, a center line calculation unit 32, and a dividing unit 33. The operation of each unit of the parameter determination device 30 is achieved by one or a plurality of processors included in a computer (not illustrated) reading and executing a computer program.

The generation unit 31 generates shape of ear hole data indicating the three-dimensional shape of the ear canal of an individual based on the data regarding the internal structure of the ear hole of an individual. The generation unit 31 is an example of a generation means. Specifically, the generation unit 31 acquires imaging data of the ear hole of an individual from the CT device, and performs image analysis on the acquired imaging data to generate shape of ear hole data indicating the three-dimensional shape of the ear canal of the individual. The generation unit 31 transmits the shape of ear hole data to the center line calculation unit 32.

The center line calculation unit 32 receives the shape of ear hole data from the generation unit 31 and calculates the center line of the ear canal based on the shape of ear hole data. The center line calculation unit 32 is an example of a center line calculation means. A method by which the center line calculation unit 32 calculates the center line of the ear canal is not particularly limited. In the first example embodiment and the following second example embodiment, different methods will be specifically described.

In the first example embodiment, the center line calculation unit 32 sets a line passing through both ends of the ear canal, divides the ear canal into a plurality of layers orthogonal to the line passing through both ends of the ear canal and each having a predetermined thickness, approximates the contour of the cross-section of the ear canal for each layer with an ellipse, and connects the center points of the plurality of ellipses (FIG. 8). As a result, the center line calculation unit 32 can obtain the center line of the ear canal. The center line calculation unit 32 transmits the calculation result of the center line of the ear canal to the dividing unit 33.

The dividing unit 33 receives the calculation result of the center line of the ear canal from the center line calculation unit 32. The dividing unit 33 divides the ear canal into a plurality of layers perpendicular to the center line, and calculates a parameter indicating the shape of the ear canal for each of the divided layers. The dividing unit 33 is an example of a dividing means. Specifically, the number (n) for identifying each layer obtained by dividing the ear canal and the size (R) of the diameter of the hole relating to the thickness of the ear canal for each layer are calculated as parameters of the ear model 20a. The dividing unit 33 transmits the calculated parameter (R, n) to the input unit 104 of the arithmetic device 10.

(Operation of Parameter Determination Device 30)

Figure 5:
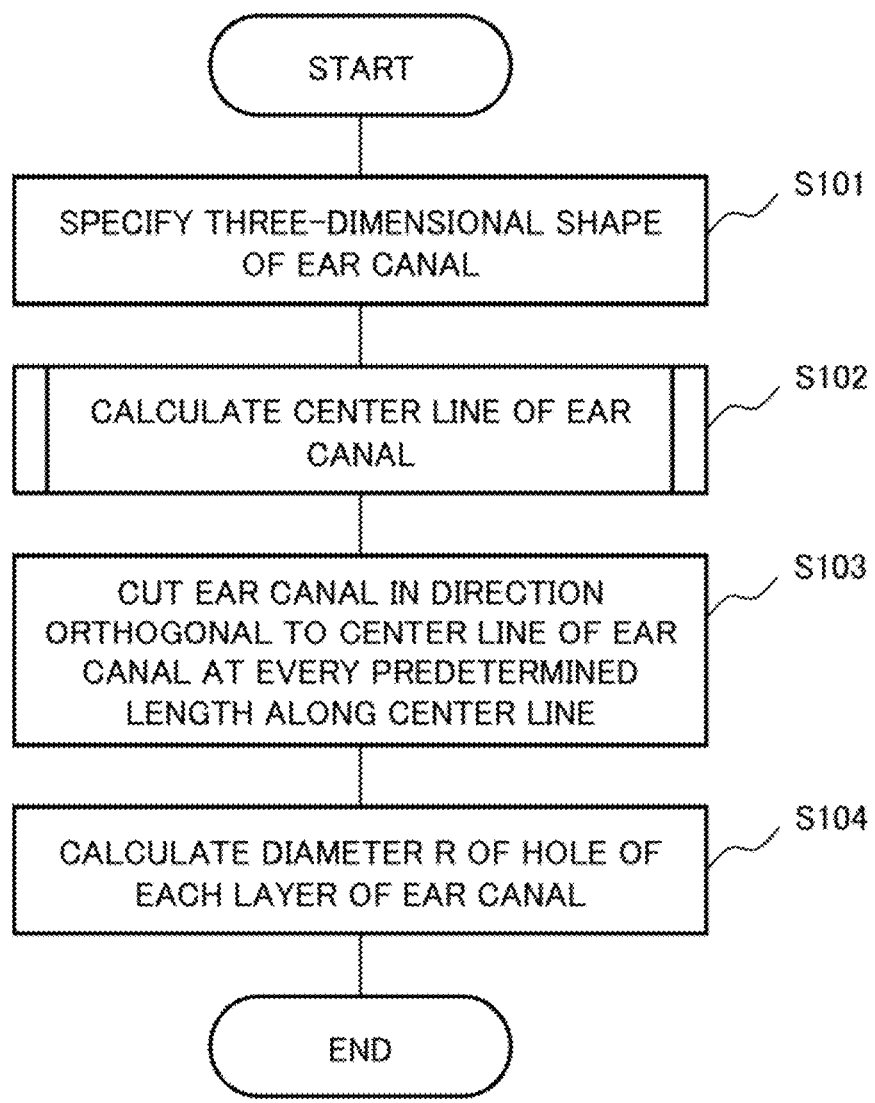
FIG. 5 is a flowchart illustrating a flow of a parameter determination method according to the first example embodiment.
Figure 6A:
FIG. 6 is a conceptual diagram for explaining a flow of a parameter determination method according to the first example embodiment.
Figure 6B:
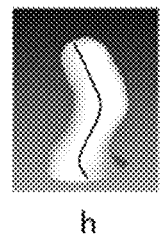
Figure 6C:
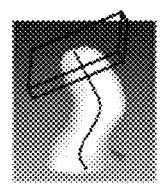
Figure 6D:
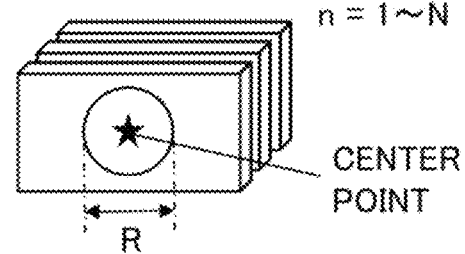

The operation of the parameter determination device 30 according to the first example embodiment will be described with reference to FIG. 5 and FIG. 6A to FIG. 6 D. FIG. 5 is a flowchart illustrating a flow of processing executed by each unit of the parameter determination device 30. FIG. 6A to FIG. 6 D are diagrams conceptually illustrating the operation of the parameter determination device 30.

First, the generation unit 31 acquires shape of ear hole data (for example, ear hole imaging data) regarding the internal structure of the ear hole of an individual. As illustrated in FIG. 5, the generation unit 31 specifies the three-dimensional shape of the ear canal of an individual by analyzing the acquired shape of ear hole data (S101).

The generation unit 31 generates shape of ear hole data indicating the three-dimensional shape of the ear canal of an individual (FIG. 6 A). Then, the generation unit 31 transmits shape of ear hole data indicating the three-dimensional shape of the ear canal of an individual to the center line calculation unit 32.

Figure 7:
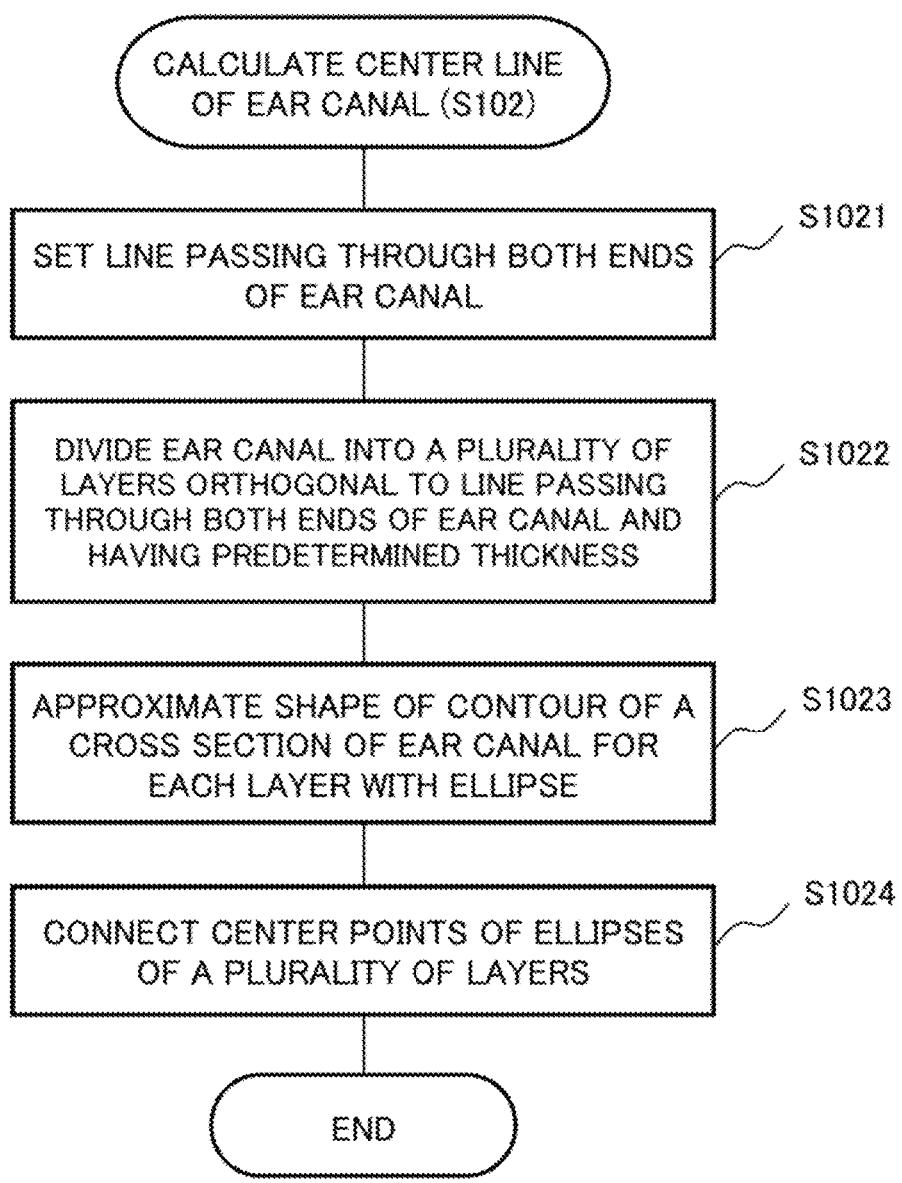
FIG. 7 is a flowchart illustrating a flow of processing of calculating a center line of an ear canal in the parameter determination method according to the first example embodiment.

The center line calculation unit 32 receives shape of ear hole data indicating the three-dimensional shape of the ear canal of an individual from the generation unit 31. The center line calculation unit 32 calculates the center line h of the ear canal using the acquired data (S102) (FIG. 6 B). Details of step S102 will be described later (FIG. 7).

The center line calculation unit 32 transmits to the dividing unit 33 the calculation result of the center line h of the ear canal together with the shape of ear hole data indicating the three-dimensional shape of the ear canal of an individual.

The dividing unit 33 receives the calculation result of the center line h of the ear canal from the center line calculation unit 32. The dividing unit 33 cuts the ear canal in a direction orthogonal to the center line h of the ear canal at every predetermined length along the center line h (S103) (FIG. 6

C). The predetermined length is equal to the thickness (FIG. 3) of one plate-shaped member 201. The predetermined length is obtained by dividing the center line h of the ear canal into N. Hereinafter, a layer from the (n−1)-th cross section to the n-th cross section of the ear canal is referred to as an n-th layer. The 0-th cross section of the ear canal relates to an end portion of the ear canal on the ear canal opening side. The N-th cross section of the ear canal relates to an end portion on the eardrum side.

The dividing unit 33 also receives shape of ear hole data indicating the three-dimensional shape of the ear canal of an individual from the center line calculation unit 32. The dividing unit 33 calculates the diameters R of the holes of the ear canal from the first layer to the N-th layer based on the shape of ear hole data indicating the three-dimensional shape of the ear canal of an individual (S104) (FIG. 6 D). The thickness R of the ear canal in the n-th layer (n=1 to N) relates to the size R (FIG. 3) of the diameter of the hole of the n-th plate-shaped member 201. Here, in a case where the shape of the cross-section of the ear canal in the n-th layer (n=1 to N) is not circular, the dividing unit 33 first approximates the contour of the cross-section of the ear canal in the n-th layer (n=1 to N) with an ellipse, and calculates a circle having an area equal to the area of the approximated ellipse. Then, the dividing unit 33 sets the calculated diameter of the circle to the thickness R of the ear canal. In order to approximate the contour of the cross section of the ear canal in the n-th layer (n=1 to N) with an ellipse, the dividing unit 33 can use a method described in "Method for calculating center line of ear canal" described later.

Thus, the operation of the parameter determination device 30 ends.

(Method for Calculating Center Line of Ear Canal)

Figure 8A:
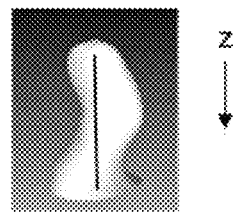
FIG. 8 is a conceptual diagram for describing a flow of processing of calculating a center line of an ear canal in the parameter determination method according to the first example embodiment.
Figure 8B:
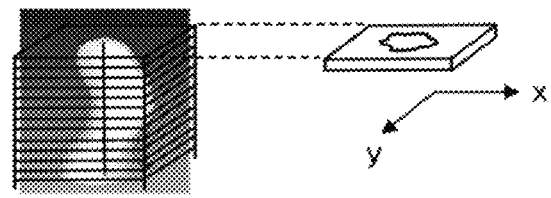
Figure 8C:
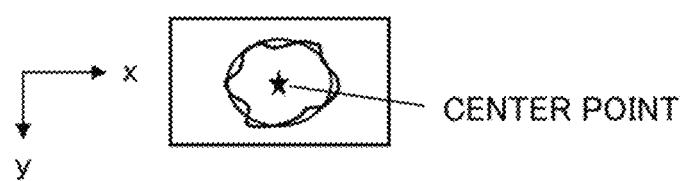
Figure 8D:
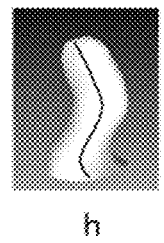

An example of a method in which the center line calculation unit 32 calculates the center line h of the ear canal will be described with reference to of FIG. 7 and FIG. 8A to FIG. 8 D. FIG. 7 is a flow relating to step S102 in FIG. 5 described above. FIG. 8A to FIG. 8 D are diagrams conceptually illustrating the flow of the operation of the center line calculation unit 32.

As illustrated in FIG. 7, the center line calculation unit 32 first sets a straight line connecting an end portion of the ear canal on the ear canal opening side and an end portion of the ear canal on the eardrum side (S1021) (FIG. 8 A). Specifically, the center line calculation unit 32 sets a straight line (z axis illustrated in FIG. 8) connecting a lower end point of the ear canal on the ear canal opening side (lower side in FIG. 6) and an upper end point of the ear canal on the eardrum side (upper side in FIG. 6).

The center line calculation unit 32 divides the ear canal into a plurality of layers orthogonal to the line passing through both ends of the ear canal set in step S1021 and having an equal thickness (that is, the length in the direction of the line passing through both ends of the ear canal) (S1022). Each layer extends in an xy plane perpendicular to the z-axis (FIG. 8 B).

The center line calculation unit 32 approximates the shape of the cross section of the ear canal with an ellipse (S1023) (FIG. 8 C). Specifically, the center line calculation unit 32 first defines a residual $r_j$ expressed by the following mathematical expression. $(x(j), y(j))$ $(j=1, 2, \ldots, 6, \ldots)$ is coordinates representing a point on the contour of the cross-section of the ear canal. The variable j represents the number of a point on the contour.

$$r_j = E_1*x(j)^2 + E_2*y(j)^2 + E_3*x(j)y(j) + E_4*x(j) + E_5*y(j) - 1 \quad \text{[Math 1]}$$

For example, the center line calculation unit 32 calculates the residual $r_j$ expressed by the above mathematical expression for each set of five coordinates $(x(j), y(j))$. Then, the center line calculation unit 32 determines a set of coefficients $E_1$ to $E_5$ in such a way that the sum of the squares of the calculated residual $r_j$ is minimized. Here, such a set of coefficients is described as $(E_{01}, E_{02}, E_{03}, E_{04}, E_{05})$. Specifically, the center line calculation unit 32 sets the partial differentiations of the functions $J(E_1, E_2, E_3, E_4, E_5)$ expressed by the following mathematical expressions with $E_1, E_2, E_3, E_4,$ and $E_5$ to 0. The center line calculation unit 32 determines the $(E_{01}, E_{02}, E_{03}, E_{04}, E_{05})$ by solving the simultaneous equations in five unknowns thus obtained.

$$\sum_{j=1}^{6} r_j^2 = \int (E_1, E_2, E_3, E_4, E_5) \quad \text{[Math 2]}$$

The center line calculation unit 32 approximates the contour of the cross-section of the ear canal with an ellipse expressed by the following equation.

$$1 = E_{01}*x^2 + E_{02}*y^2 + E_{03}*xy + E_{04}*x + E_{05}*y \quad \text{[Math 3]}$$

The center line calculation unit 32 calculates the center point of the ellipse based on the above equation. The center line calculation unit 32 calculates an ellipse that approximates the shape of the cross-section of the ear canal and the center point thereof for each layer in this manner, and then connects the calculated center points (S1024). As a result, the center line h of the ear canal is obtained (FIG. 8 (b-4)).

The description of the example of the operation of the center line calculation unit 32 in step S102 of FIG. 5 is terminated.

(Arithmetic Device 10)

Figure 9:
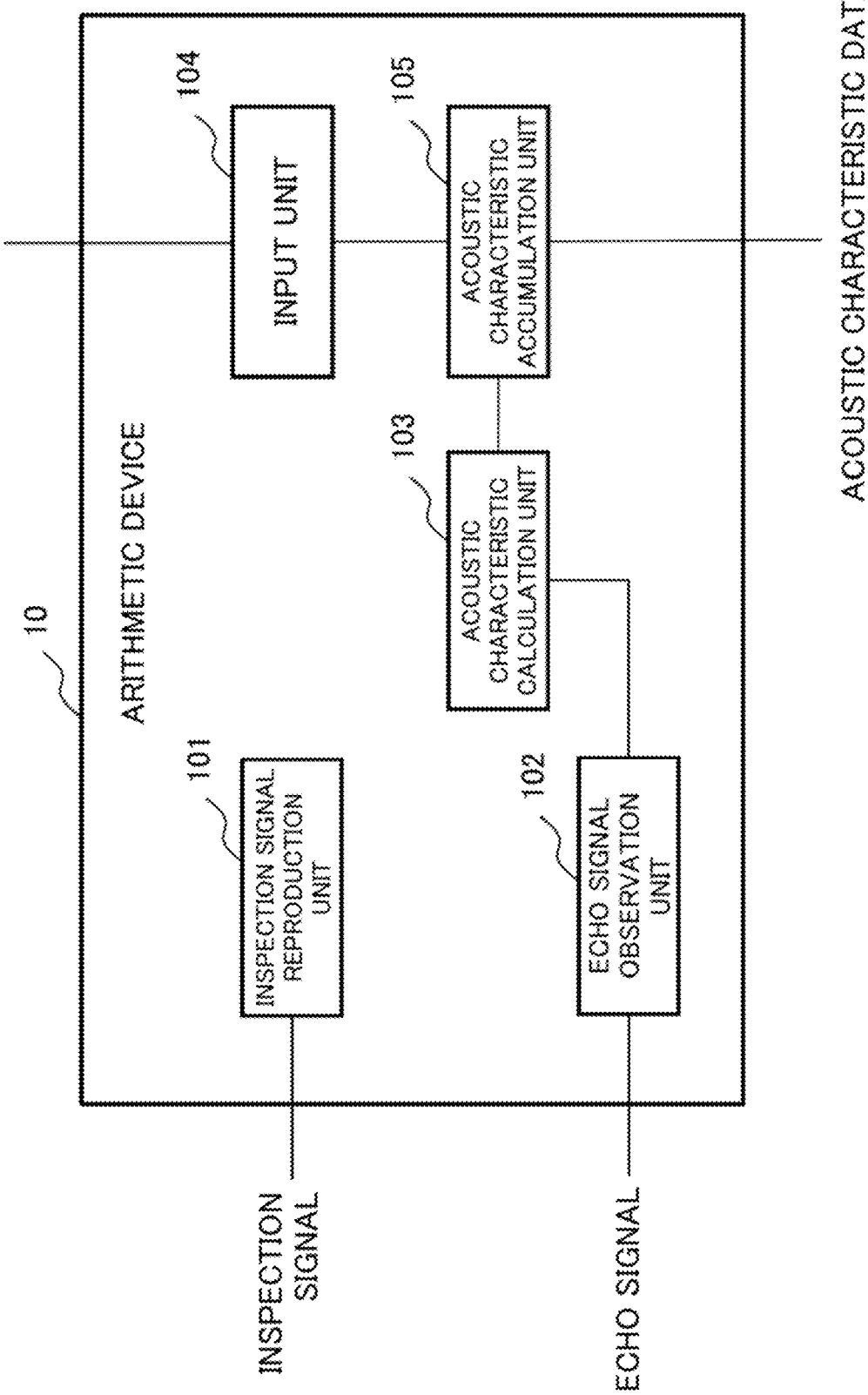
FIG. 9 is a block diagram illustrating a configuration of an arithmetic device included in the system according to the first example embodiment.

A configuration of the arithmetic device 10 according to the first example embodiment will be described with reference to FIG. 9. FIG. 9 is a block diagram illustrating a configuration of the arithmetic device 10. As illustrated in FIG. 9, the arithmetic device 10 includes an inspection signal reproduction unit 101, an echo signal observation unit 102, an acoustic characteristic calculation unit 103, an input unit 104, and an acoustic characteristic accumulation unit 105.

The inspection signal reproduction unit 101 reproduces the inspection signal input to the ear model 20a. The inspection signal input to the ear model 20a echoes inside the hole of the ear model 20a, and echo sounds are output from the ear model 20a. Data obtained by encoding the inspection signal reproduced by the inspection signal reproduction unit 101 is stored in advance in a recording medium (not illustrated). Inspection signal reproduction unit 101 acquires the data of the inspection signal stored in the recording medium, and reproduces the inspection signal. How to determine the inspection signal is not particularly limited. For example, the inspection signal is experimentally determined based on the general thickness and length of the ear holes of a plurality of individuals such that echo sound from the ear holes of any individual is strong (or S/N is large).

The echo sound indicates a characteristic depending on the internal structure of the hole of the ear model 20a (referred to as an acoustic characteristic of the ear model 20a). The acoustic characteristics of the ear model 20a relate to the acoustic characteristics of the ear hole of an individual simulated by the hole of the ear model 20a. Since the internal structure of the ear hole of the individual has individuality, it is possible in principle to identify the individual based on the acoustic characteristic of the ear hole of the individual.

Inspection signal reproduction unit 101 transmits the reproduced inspection signal to the earphone-type device 40 in a wireless or wired manner, and causes the speaker of the earphone-type device 40 to output the inspection signal. Specifically, the inspection signal is an impulse wave.

The echo signal observation unit 102 observes the echo signal based on the echo sound from the ear model 20a using the microphone of the earphone-type device 40. More specifically, after the inspection signal propagates in the ear model 20a, an echo sound is output from the ear model 20a. The microphone of the earphone-type device 40 collects the echo sound output from the ear model 20a. The earphone-type device 40 generates an echo signal by converting the echo sound collected by the microphone into digital data.

The echo signal observation unit 102 requests an echo signal from the earphone-type device 40. The earphone-type device 40 transmits an echo signal to the echo signal observation unit 102 in a wireless or wired manner. The echo signal observation unit 102 receives the echo signal from the earphone-type device 40 in a wireless or wired manner. The echo signal observation unit 102 transmits the echo signal received from the earphone-type device 40 to the acoustic characteristic calculation unit 103.

The acoustic characteristic calculation unit 103 receives the echo signal from the echo signal observation unit 102. The acoustic characteristic calculation unit 103 calculates a transfer function as the acoustic characteristic of the ear model 20a from the received echo signal. That is, the transfer function is an example of the acoustic characteristic. A response function indicating a response (echo sound) of the ear model 20a to the inspection signal is another example of the acoustic characteristic.

Specifically, the acoustic characteristic calculation unit 103 first extracts an impulse response from the echo signal. The impulse response is a response (echo sound) of the ear model 20 to the inspection signal that is an impulse wave. The acoustic characteristic calculation unit 103 calculates a transfer function by performing Fourier transform or Laplace transform on the impulse response. The acoustic characteristic calculation unit 103 transmits data of the calculated transfer function to the acoustic characteristic accumulation unit 105.

The input unit 104 acquires the size (R) of the diameter of the hole provided at the center of each plate-shaped member 201 (FIG. 4) and the number (n) indicating the arrangement order of the plate-shaped members 201 as parameters of the ear model 20a. Specifically, the input unit 104 acquires the parameter (R, n) of the ear model 20a from the dividing unit 33 of the parameter determination device 30.

The input unit 104 transmits information indicating the parameter (R, n) of the ear model 20a to the acoustic characteristic accumulation unit 105.

The acoustic characteristic accumulation unit 105 receives the data of the transfer function from the acoustic characteristic calculation unit 103. In addition, the acoustic characteristic accumulation unit 105 receives information indicating the parameter (R, n) of the ear model 20a from the input unit 104. The acoustic characteristic accumulation unit 105 accumulates the data of the transfer function received from the acoustic characteristic calculation unit 103 and information indicating the parameter (R, n) of the ear model 20a in association with each other in a recording medium not illustrated as acoustic characteristic data.

(Example of Acoustic Characteristic Data)

FIG. 10 is an example of the acoustic characteristic data stored in the recording medium by the acoustic characteristic accumulation unit 105. As illustrated in FIG. 10, the acoustic characteristic data includes the parameter (R, n) of the ear model 20 and data of a transfer function. As described above, the parameter (R, n) is the size (R) of the diameter of the hole of the plate-shaped member 201 and the number (n) of the plate-shaped member 201. The acoustic characteristic accumulation unit 105 generates acoustic characteristic data illustrated in FIG. 10 for each of the plurality of ear models 20 having different parameter (R, n).

Effects of Example Embodiment

According to the configuration of the embodiment, the generation unit 31 generates shape of ear hole data indicating a three-dimensional shape of an ear canal of an individual based on the data related to the internal structure of the ear hole of an individual, the center line calculation unit 32 calculates the center line of the ear canal, and the dividing unit 33 divides the ear canal into a plurality of layers perpendicular to the center line, and calculates a parameter indicating the shape of the ear canal for each of the divided layers.

Specifically, the parameter indicating the shape of the ear canal is the number for identifying each layer obtained by dividing the ear canal and the size of the diameter of the hole relating to the thickness of the ear canal for each layer. By manufacturing the plurality of plate-shaped members 201 relating to the plurality of layers of the ear canal, the ear model 20a configured by the plurality of plate-shaped members 201 can be easily manufactured. Using the manufactured ear model 20a, it is possible to easily evaluate the performance of the earphone-type device 40 used for the otoacoustic authentication at low cost.

Second Example Embodiment

Figure 11:
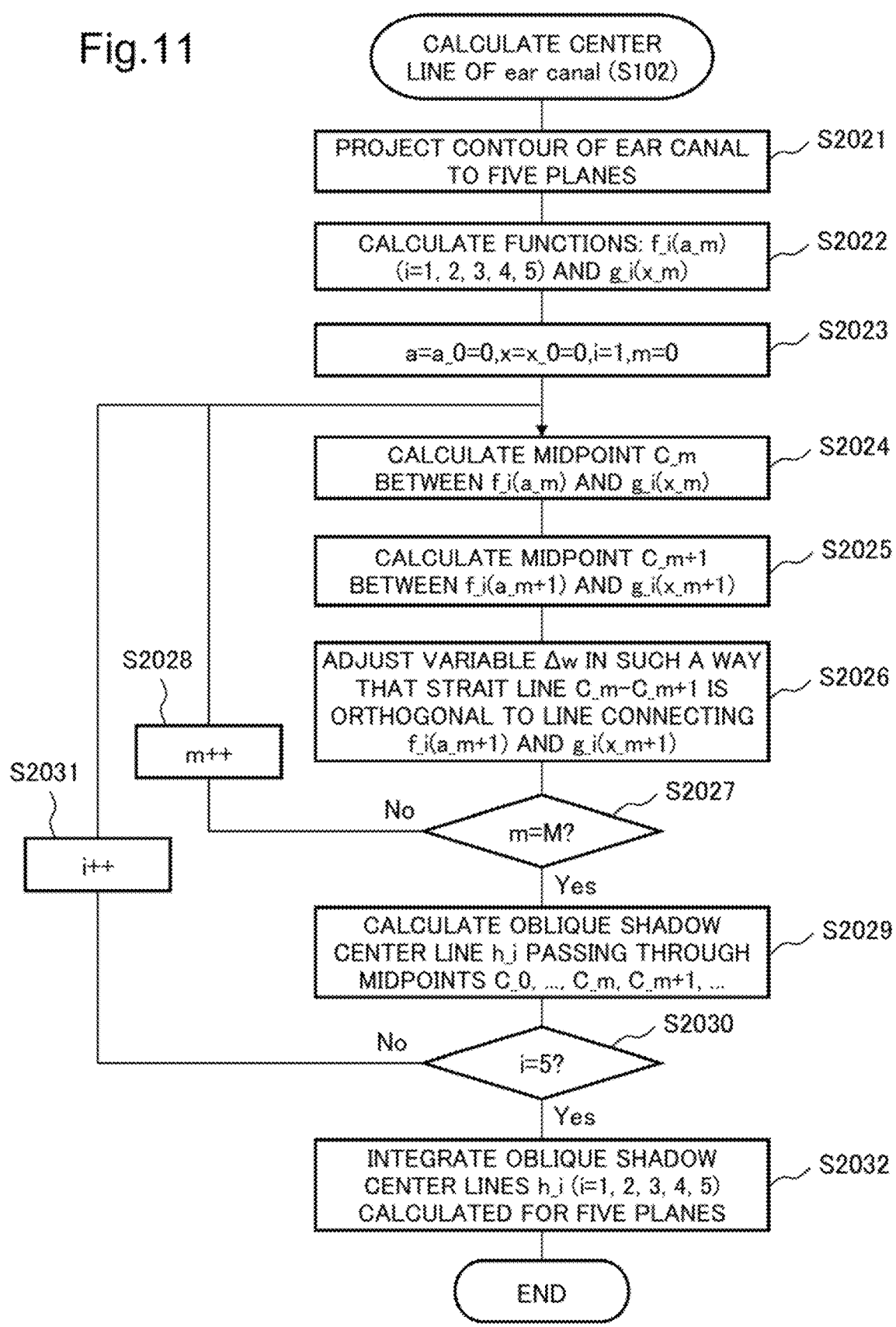
FIG. 11 is a flowchart illustrating a flow of processing of calculating the center line of the ear canal in the parameter determination method according to a second example embodiment.

The second example embodiment will be described with reference to FIGS. 11 to 13. In the second example embodiment, processing different from the processing of calculating the center line of the ear canal described in the first example embodiment (FIG. 7) will be described.

Since the configurations of the system 1 and the parameter determination device 30 according to the second example embodiment are the same as those of the first example embodiment, the description thereof will be omitted in the second example embodiment.

(Method for Calculating Center Line of Ear Canal)

An example of a method by which the center line calculation unit 32 calculates the center line of the ear canal will be described with reference to FIGS. 11 to 13. FIG. 11 is a flow relating to step S102 in FIG. 5 described in the first example embodiment. (b'-1) to (b'-3) of FIG. 12 are diagrams conceptually illustrating the flow of the operation of the center line calculation unit 32. FIG. 13 illustrates a contour of the ear canal projected with respect to one plane. In FIGS. 11 to 13, letters written after the underbar ("_") represent subscripts.

Although not illustrated, the center line calculation unit 32 first sets a reference line connecting an end portion of the ear canal on the ear canal opening side and an end portion of the ear canal on the eardrum side as in step S1021 (FIG. 7) described in the first example embodiment.

Figure 12:
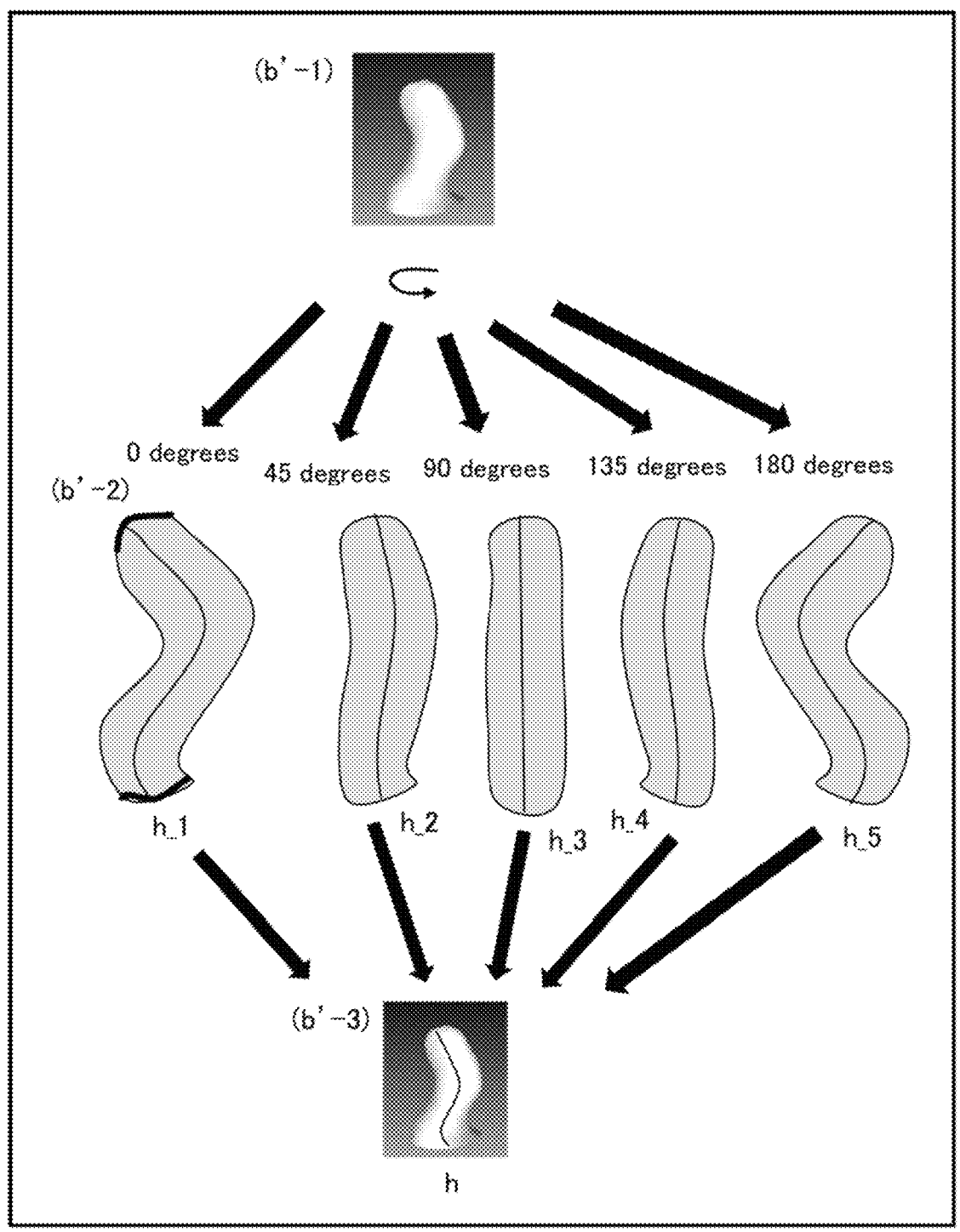
FIG. 12 is a conceptual diagram for describing a flow of processing of calculating the center line of the ear canal in the parameter determination method according to the second example embodiment.

The center line calculation unit 32 projects the contour of the ear canal onto five planes parallel to the line connecting the end of the ear canal on the ear canal opening side and the end on the eardrum side (S2021) ((b'-1) of FIG. 12).

The center line calculation unit 32 sets one plane passing through the reference line and parallel to the reference line as a reference plane. The center line calculation unit 32 projects the contour of the ear canal onto five planes having 0 degrees, 45 degrees, 90 degrees, 135 degrees, and 180 degrees with respect to the reference plane, and calculates functions: $f_i(a)$ and $g_i(x)$ (i=1 to 5) indicating two portions excluding the end on the ear canal opening side and the end on the eardrum side from the projected contour of the ear canal (S2022) ((b'-2) of FIG. 12 and FIG. 13). $f_i(a)$ and $g_i(x)$ (i=1 to 5) are coordinates on a plane representing points on the contour of the ear canal projected onto the plane.

The variable a is a variable indicating a length measured in a direction from the end on the eardrum side toward the end on the ear canal opening side along the left contour line of the ear canal projected on the plane. The variable x is a variable indicating a length measured in a direction from the end on the eardrum side toward the end on the ear canal opening side along the right contour line of the ear canal projected on the plane. m is a subscript (number) of the coordinates $C_m$.

Figure 13:
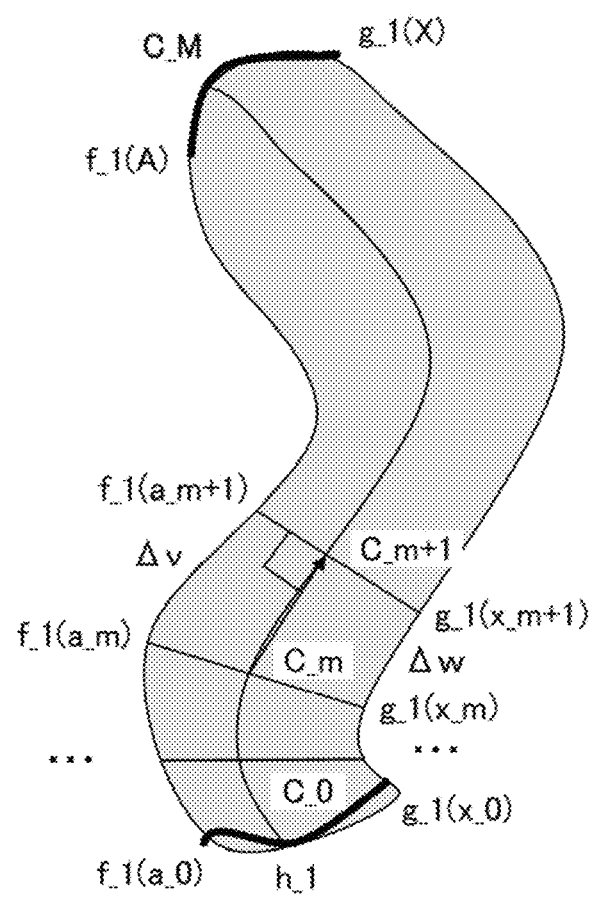
FIG. 13 is another diagram for explaining the flow of processing of calculating the center line of the ear canal in the parameter determination method according to the second example embodiment.

As illustrated in FIG. 13, m is an integer from 0 to M. The coordinates $C_m$ represent coordinates on the center line of the ear canal projected onto the plane. It is assumed that $a=a_m$ and $x=x_m$ are positions where a line passing through the coordinates $C_m$ and orthogonal to the center line of the ear canal projected onto the plane intersects with the left contour line ($f_i$) of the ear canal and the right contour line ($g_i$) of the ear canal, respectively. The variable a takes $a_0$, $a_1$, $a_2$, ..., $a_m$, ..., A ($=a_M$). The variable x takes $x_0$, $x_1$, $x_2$ ..., $x_m$, X ($=X_M$). $a_m$ is expressed as $a_m=a_{m-1}+\Delta v$. In addition, $x_m=x_{m-1}+\Delta w$. $\Delta v$ is a fixed value, but $\Delta w$ is variable.

0 is stored in the variable m, and 1 is stored in the variable i (S2023). It is assumed that the values of variables a and x at the end of the ear canal on the eardrum side (lower side in FIG. 13) are $a=a_0=0$ and $x=x_0=0$, respectively.

The center line calculation unit 32 calculates coordinates $C_m$ indicating the position of the midpoint between $f_i(a_m)$ and $g_i(x_m)$ (S2024).

Next, the center line calculation unit 32 calculates $f_i(a_{m+1})=f_i(a_m+\Delta v)$. Further, the center line calculation unit 32 calculates $g_i(x_{m+1})=g_i(x_m+\Delta w)$. Then, the center line calculation unit 32 provisionally calculates coordinates $C_{m+1}$ indicating the position of the midpoint between $f_i(a_{m+1})$ and $g_i(x_{m+1})$ (S2025). The coordinates $C_{m+1}$ are determined according to $\Delta w$.

The center line calculation unit 32 adjusts the variable $\Delta w$ in such a way that a line connecting $f_i(a_{m+1})$ and $g_i(x_{m+1})$ is orthogonal to the straight line $C_{m+1}$-$C_m$ (that is, a straight line connecting the two midpoints $C_m$ and $C_{m+1}$, and is indicated by an arrow in FIG. 13) (S2026).

Thereafter, the center line calculation unit 32 determines coordinates $C_{m+1}$ indicating the position of the midpoint between $f_i(a_m+\Delta v)$ and $g_i(x_m+\Delta w)$ ($\Delta w$ is an adjusted value). When the variable m is not M (No in S2027), 1 is added to the variable m (S2028), and the flow returns to step S2024.

On the other hand, when the variable m is M (Yes in S2027), the center line calculation unit 32 calculates the oblique shadow center line $h_i$ passing through $C_0$, ..., $C_m$, $C_{m+1}$, ..., and $C_M$ (S2029). Thereafter, the flow proceeds to step S2030. The oblique shadow center line $h_i$ is obtained by connecting $C_m$ from $C_0$ to $C_M$ in ascending or descending order of m.

In a case where the variable m is M (Yes in S2027) and the variable i is not equal to 5 (No in S2030), 1 is added to the variable i (S2031), and the flow returns to step S204.

When the variable m is M (Yes in S2027) and the variable i is equal to 5 (Yes in S2030), the center line calculation unit 32 integrates the oblique shadow center lines $h_i$ (i=1, 2, 3, 4, and 5) calculated for the five planes (S2032) ((b'-3) of FIG. 12).

Specifically, the center line calculation unit 32 sets the z axis along the reference axis in the cylindrical coordinate system centered on the reference line. The coordinates on the five oblique shadow center lines $h_i$ (i=1, 2, 3, 4, and 5) calculated by the center line calculation unit 32 are written as ($z$, $c_i$). Here, $c_i$ is coordinates indicating a position on the oblique shadow center line $h_i$ in a direction orthogonal to the reference line. At this time, the center line calculation unit 32 defines the residual $s_i$ expressed by the following mathematical expression.

$$s_1 = r(z)\cos 0° + R(z)\sin 0° - c_1$$

$$s_2 = r(z)\cos 45° + R(z)\sin 45° - c_2$$

$$s_3 = r(z)\cos 90° + R(z)\sin 90° - c_3$$

$$s_4 = r(z)\cos 135° + R(z)\sin 135° - c_4$$

$$s_5 = r(z)\cos 180° + R(z)\sin 180° - c_5 \quad \text{[Math 4]}$$

The center line calculation unit 32 determines the coefficients r and R in such a way that the sum of the squares of the calculated residuals ($s_1$, $s_2$, $s_3$, $s_4$, $s_5$) is minimized. Here, such a set of coefficients is described as ($r_0$, $R_0$). Specifically, ($r_0$, $R_0$) minimizes the sum expressed by the following mathematical expression.

$$\sum_{i=1}^{5} s_i^2 \quad \text{[Math 5]}$$

The coordinates on the center line h in the three-dimensional space are expressed as ($r_0(z)$, $R_0(z)$, $z$). In this manner, the center line calculation unit 32 calculates the center line h of the ear canal from the oblique shadow center line $h_i$ (i=1, 2, 3, 4, and 5).

As described above, the description of the example of the process in which the center line calculation unit 32 calculates the center line h of the ear canal in step S102 of FIG. 5 ends.

Effects of Example Embodiment

According to the configuration of the embodiment, the generation unit 31 generates shape of ear hole data indicating a three-dimensional shape of an ear canal of an individual based on the data related to the internal structure of the ear hole of an individual, the center line calculation unit 32 calculates the center line of the ear canal, and the dividing unit 33 divides the ear canal into a plurality of layers perpendicular to the center line, and calculates a parameter indicating the shape of the ear canal for each of the divided layers.

Specifically, the parameter indicating the shape of the ear canal is the number for identifying each layer obtained by dividing the ear canal and the size of the diameter of the hole relating to the thickness of the ear canal for each layer. The ear model 20a can be easily manufactured by manufacturing the plurality of plate-shaped members 201 relating to the plurality of layers of the ear canal. Using the manufactured ear model 20a, it is possible to easily evaluate the performance of the earphone-type device 40 used for the otoacoustic authentication at low cost.

Furthermore, as an example is described in the example embodiment, the center line calculation unit 32 can calculate the center line of the ear canal by various methods.

(Hardware Configuration)

Figure 14:
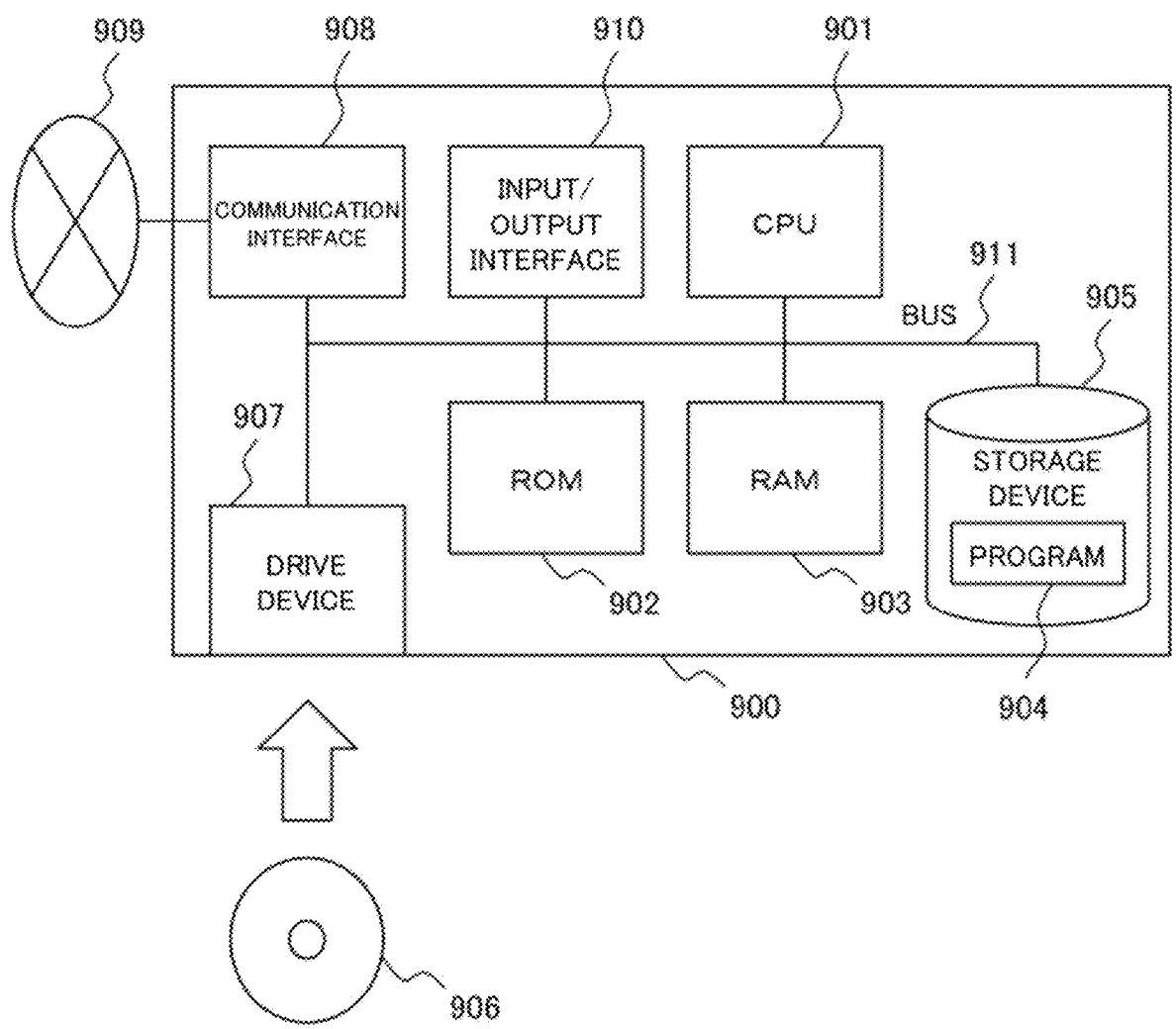
FIG. 14 is a diagram illustrating a hardware configuration of the parameter determination device according to the first or second example embodiment.

Each component of the parameter determination device 30 described in the first example embodiment and the second example embodiment indicates a block of a functional unit. Some or all of these components are implemented by an information processing device 900 as illustrated in FIG. 14, for example. FIG. 14 is a block diagram illustrating an example of a hardware configuration of the information processing device 900.

As illustrated in FIG. 14, the information processing device 900 includes the following configuration as an example.

CPU (Central Processing Unit) 901
    ROM (Read Only Memory) 902
    RAM (Random Access Memory) 903
    Program 904 loaded into RAM 903
    Storage device 905 storing program 904
    Drive device 907 that reads and writes recording medium 906
    Communication interface 908 connected to communication network 909
    Input/output interface 910 for inputting/outputting data
    Bus 911 connecting each component The components of the parameter determination device 30 described in the first example embodiment and the second example embodiment are implemented by the CPU 901 reading and executing the program 904 that implements these functions. The program 904 for achieving the function of each component is stored in the storage device 905 or the ROM 902 in advance, for example, and the CPU 901 loads the program into the RAM 903 and executes the program as necessary. The program 904 may be supplied to the CPU 901 via the communication network 909, or may be stored in advance in the recording medium 906, and the drive device 907 may read the program and supply the program to the CPU 901.

Effects of Example Embodiment

According to the configuration of the example embodiment, the parameter determination device 30 described in the above example embodiment is achieved as hardware. Therefore, effects similar to the effects described in the first example embodiment and the second example embodiment can be obtained.

Although the disclosure is described with reference to the example embodiments (and examples), the disclosure is not limited to the above example embodiments (and examples). Various modifications that can be understood by those skilled in the art can be made to the configuration and details of the embodiments (and examples) within the scope of the disclosure.

REFERENCE SIGNS LIST 1 system
20 (20a) ear model
30 parameter determination device
31 generation unit
32 center line calculation unit
33 dividing unit
40 earphone-type device

What is claimed is:

1. A parameter determination device comprising:
    a memory storing instructions data; and
    at least one processor configured to execute the instructions to perform:
    generating, based on data regarding an internal structure of an ear hole of an individual, shape of ear hole data indicating a three-dimensional shape of an ear canal of the individual;
    calculating a center line of the ear canal based on the shape of ear hole data, by calculating a line connecting respective center points of ellipses approximating two-dimensional shapes of cross sections of the ear canal as the center line of the ear canal;
    dividing the ear canal into a plurality of layers perpendicular to the center line; and
    calculating a parameter indicating a shape of the ear canal for each of the divided layers.

2. The parameter determination device according to claim 1, wherein
    the at least one processor is configured to execute the instructions to perform:
    calculating, as the parameter, a number for identifying each layer obtained by dividing the ear canal and a size of a diameter of a hole relating to a thickness of the ear canal for each layer.

3. A parameter determination method performed by a computer and comprising:
    generating, based on data regarding an internal structure of an ear hole of an individual, shape of ear hole data indicating a three-dimensional shape of an ear canal of the individual;
    calculating a center line of the ear canal based on the shape of ear hole data, by calculating a line connecting respective center points of ellipses approximating two-dimensional shapes of cross sections of the ear canal as the center line of the ear canal;
    dividing the ear canal into a plurality of layers perpendicular to the center line; and
    calculating a parameter indicating a shape of the ear canal for each of the divided layers.

4. The parameter determination method according to claim 3, wherein
    calculating the center line of the ear canal comprises:
    setting a straight line passing through both ends of the ear canal;
    dividing the ear canal into a plurality of layers orthogonal to the straight line passing through both ends of the ear canal, each of the plurality of layers having a predetermined thickness;
    approximating a contour of a cross section of the ear canal for each layer with an ellipse; and
    connecting respective center points of ellipses of the plurality of layers.

5. A non-transitory recording medium storing a program executable by a computer to perform processing comprising:
    generating, based on data regarding an internal structure of an ear hole of an individual, shape of ear hole data indicating a three-dimensional shape of an ear canal of the individual;
    calculating a center line of the ear canal based on the shape of ear hole data, by calculating a line connecting respective center points of ellipses approximating two-dimensional shapes of cross sections of the ear canal as the center line of the ear canal;

dividing the ear canal into a plurality of layers perpendicular to the center line;

calculating a parameter indicating a shape of the ear canal for each of the divided layers.

6. The recording medium according to claim 5, wherein calculating the center line of the ear canal comprises setting a straight line passing through both ends of the ear canal;

a step of dividing the ear canal into a plurality of layers orthogonal to the straight line passing through both ends of the ear canal, each of the plurality of layers having a predetermined thickness;

approximating a contour of a cross section of the ear canal for each layer with an ellipse; and connecting respective center points of ellipses of the plurality of layers.

\* \* \* \* \*